Figure 1:
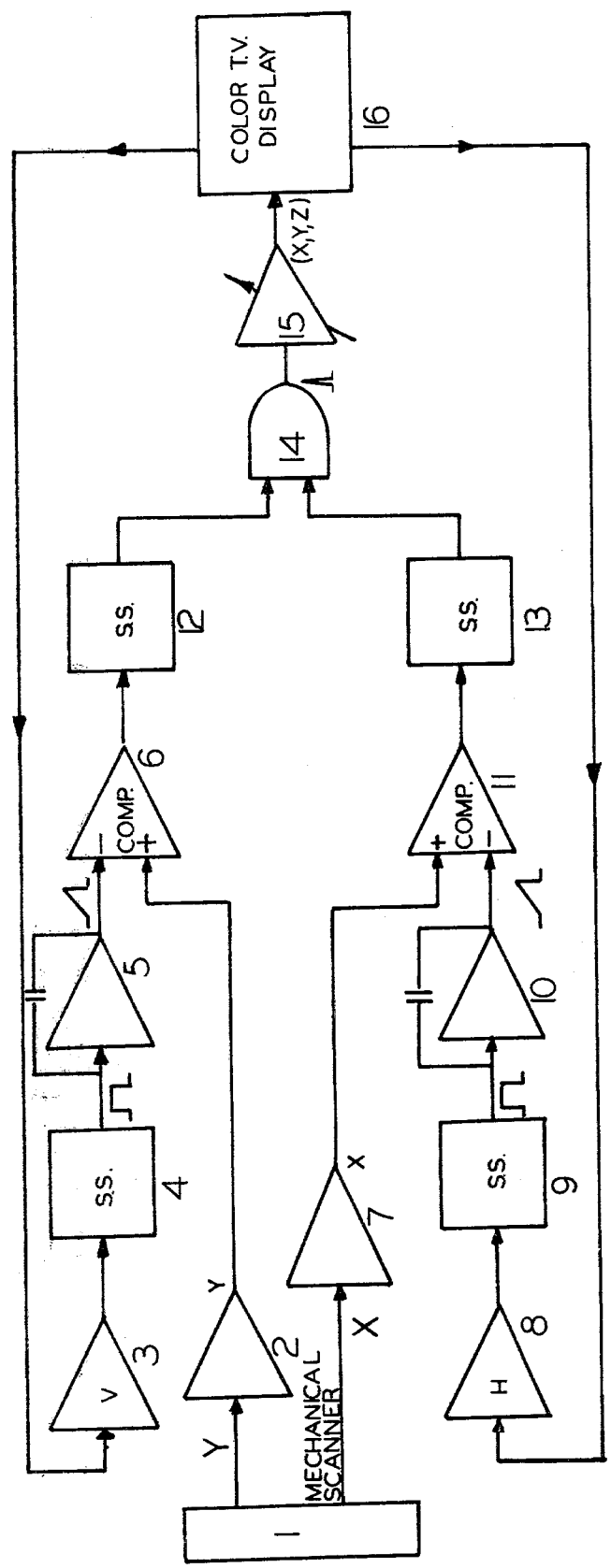

United States Patent [19]

White et al.

[11] 4,205,687

[45] Jun. 3, 1980

[54] COLOR CODED BLOOD FLOW VELOCITY DISPLAY EQUIPMENT

[75] Inventors: Denis N. White; George R. Curry, both of Kingston, Canada

[73] Assignee: Diagnostic Electronics Corporation, Lexington, Mass.

[21] Appl. No.: 820,546

[22] Filed: Jul. 29, 1977

[51] Int. Cl.[2] ............................................. A61B 10/00
[52] U.S. Cl. .................................. 128/663; 73/194 A
[58] Field of Search ............. 128/2 V, 2.05 Z, 2.05 F, 128/664, 663; 73/619–626, 194 A; 340/5 MP, 15.5 VD; 343/5 CD; 358/81–82, 98, 111–113, 105–107

[56] References Cited

U.S. PATENT DOCUMENTS

| | | | |
|---|---|---|---|
| 2,804,500 | 8/1957 | Giacoletto | 173/1 X |
| 3,156,110 | 11/1964 | Clynes | 128/2 V |
| 3,443,433 | 5/1969 | Liston et al. | 73/194 A |
| 3,581,192 | 5/1971 | Miora et al. | 324/77 |
| 3,587,298 | 6/1971 | Jacobs | 343/5 CD |
| 3,614,720 | 10/1971 | Ludlum | 343/5 CD |
| 3,617,997 | 11/1971 | Maass | 343/5 CD |
| 3,627,912 | 12/1971 | Hearn | 178/5.4 R |
| 3,675,192 | 7/1972 | Fahrbach | 340/3 D |
| 3,711,822 | 1/1973 | Muller | 343/5 CD |
| 3,723,652 | 3/1973 | Alles et al. | 179/1 VS X |
| 3,777,740 | 12/1973 | Hokanson | 128/2 V |
| 3,781,785 | 12/1973 | Balch | 340/15.5 DS |
| 3,849,793 | 11/1974 | Ablett | 358/81 |
| 3,886,489 | 2/1974 | Jones | 343/5 CD |
| 3,896,788 | 7/1975 | Sato | 128/2.05 F |
| 3,901,077 | 8/1975 | McCarty et al. | 73/194 A |
| 3,909,771 | 9/1975 | Pickering et al. | 73/620 |
| 3,918,025 | 7/1974 | Koshikawa et al. | 73/626 |
| 3,922,911 | 12/1975 | Groves et al. | 73/194 A |
| 3,961,306 | 6/1976 | Anstey | 340/15.5 DS |
| 3,987,673 | 10/1976 | Hansen | 73/194 A |
| 4,026,144 | 5/1977 | Gericke et al. | 340/5 MP |
| 4,109,642 | 8/1978 | Reid et al. | 128/2 V |

OTHER PUBLICATIONS

Andrews, H. C. et al, "Image Processing by Dig. Computer", IEEE Spectrum, Jul. 1972, pp. 20–32.
Yohoi, H. et al, "UTS Diagnostic Equipment with Color Display Unit for Simultaneous Tomogram Method"–Toshiba Review (Jap. #76, Dec. 1972), pp. 14–21.
Carter, C. R. et al, "A Color–Coded Display for Signals from Radar & Sonar", Canadian Comm. & Power Conf., Montreal 20-22 Oct. 1976, pp. 45–48.
Ito, K. et al, "Digital Image Processing of Ultrasonography", JEE, No. 115, pp. 47–50, Jul. 1976.

*Primary Examiner*—Robert W. Michell
*Assistant Examiner*—Francis J. Jaworski

[57] ABSTRACT

A method and apparatus are disclosed for providing a picture of a portion of a blood vessel by a color coded display of normal and increased blood flow peak velocities at a plurality of locations within the blood vessel portion from ultrasonic doppler velocity signals proportional to blood flow velocity within the blood vessel.

Velocity signals below a predetermined minimum are rejected. Velocity signals above the predetermined minimum are separated into a plurality of selected ranges representing normal and increased blood flow peak velocity ranges. Each of these normal and increased blood flow peak velocity ranges is then displayed as a discrete color.

5 Claims, 3 Drawing Figures

COLOR CODED BLOOD FLOW VELOCITY DISPLAY EQUIPMENT

This invention relates to blood flow velocity display equipment for providing a picture of blood flow velocity at a plurality of locations within a blood vessel and, more particularly, to equipment for displaying color coded peak blood flow velocities.

It is well recognized that one of the most common causes of death and crippling diseases is the occlusion of arteries supplying blood to the tissues of organs such as the brain or heart. Early detection of stenosis, or vessel narrowing, can frequently permit corrective treatment. Whenever possible a non-invasive diagnostic procedure is desirable rather than intrusive contrast studies using X-ray imaging.

In recent years, ultrasound has come into use as a tool for the study of blood vessel flow because the transmitted energy is back-scattered with shifted frequency by red cells moving in the blood stream. The most common instruments make use of this doppler principle by producing an audible tone, and often a chart record, proportional to the instantaneous average blood velocity.

Recently Reid and Spencer, (1972) *Ultrasonic Doppler Technique for Imaging Blood Vessels,* Science 176:1235–1236, and see also *Ultrasound in Medicine,* Vol. 3B, Plenum Press, N.Y., 1977, introduced spatial information by attaching a position-sensor to a doppler transducer to produce an image of the blood flow in the carotid arteries. Such equipment is presently commercially available from Carolina Medical Electronics, Inc., King, N.C. However that system has features which limits its clinical usefulness; for example, it is equally sensitive to all echo-frequencies above a preset threshold restricting its response to the presence or absence of flow and its response to the narrowing of a vessel lumen is a narrowing of the image. Because the ultrasound beam width is large, a small region of stenosis, even if severe, can be represented by an image only slightly narrower than regions with normal flow.

It is a major object of the present invention to circumvent these restrictions and provide improved equipment.

Accordingly, the present invention provides blood flow velocity display equipment for providing a picture of a portion of a blood vessel by the color coded display of normal and increased blood flow peak velocity at a plurality of locations within a blood vessel. It includes ultrasonic doppler scanning means providing location signals and a velocity signal proportional to blood flow velocity at a location. It uniquely provides peak velocity filter means for rejecting velocity signals below a predetermined minimum and separating velocity signals above the predetermined minimum into a plurality of selected ranges providing a plurality of independent filter means output signals representing normal and increased blood flow peak velocity ranges and color coding means for providing a discrete color signal for each of the filter means output signals. Display means are provided responsive to the location signals and color signals for displaying the color coded picture with each of the normal and increased blood flow peak velocity ranges displayed as a discrete color. Preferably, the peak velocity filter means predetermined minimum represents less than normal blood flow peak velocity and its ranges represent normal, moderately increased and markedly increased blood flow peak velocity ranges and the display means displays each as a discrete color, the less than normal blood flow peak velocity being characterized by the absence of a display.

Figure 2:
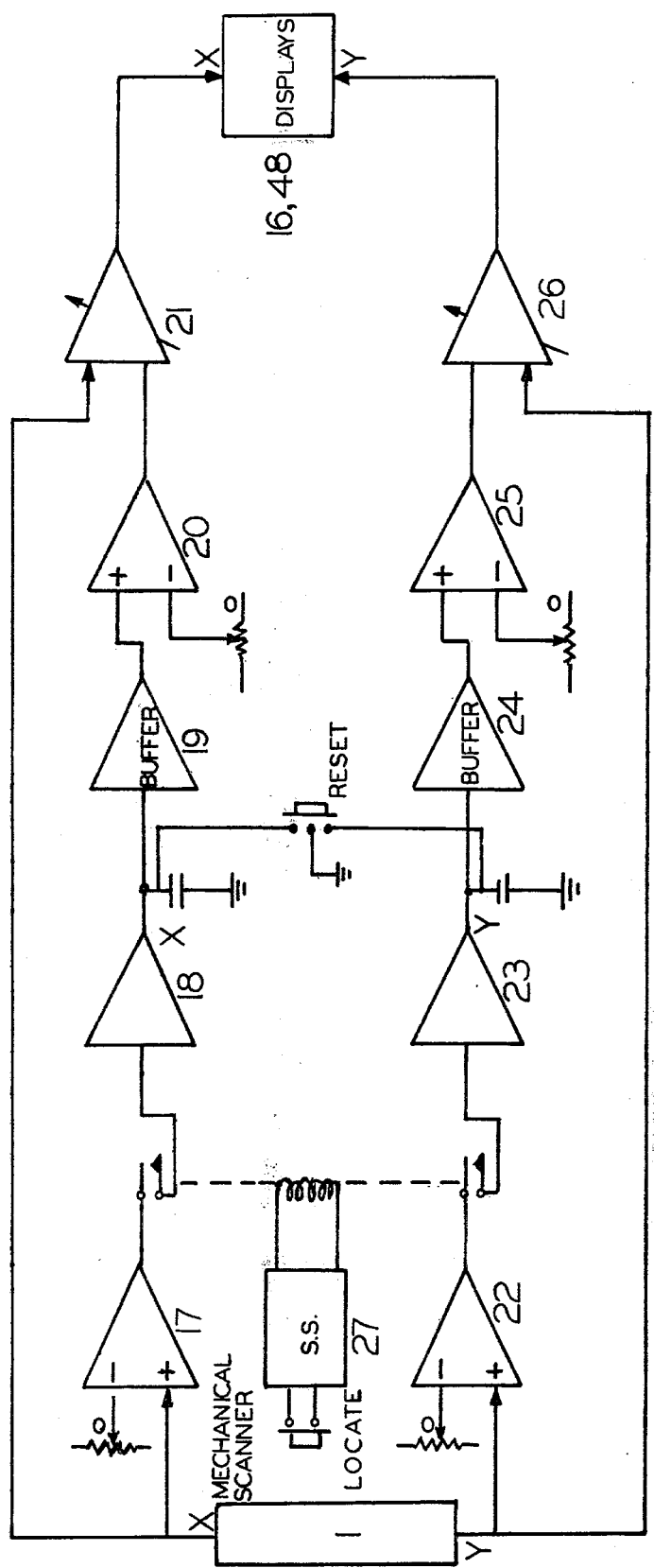
Figure 3:
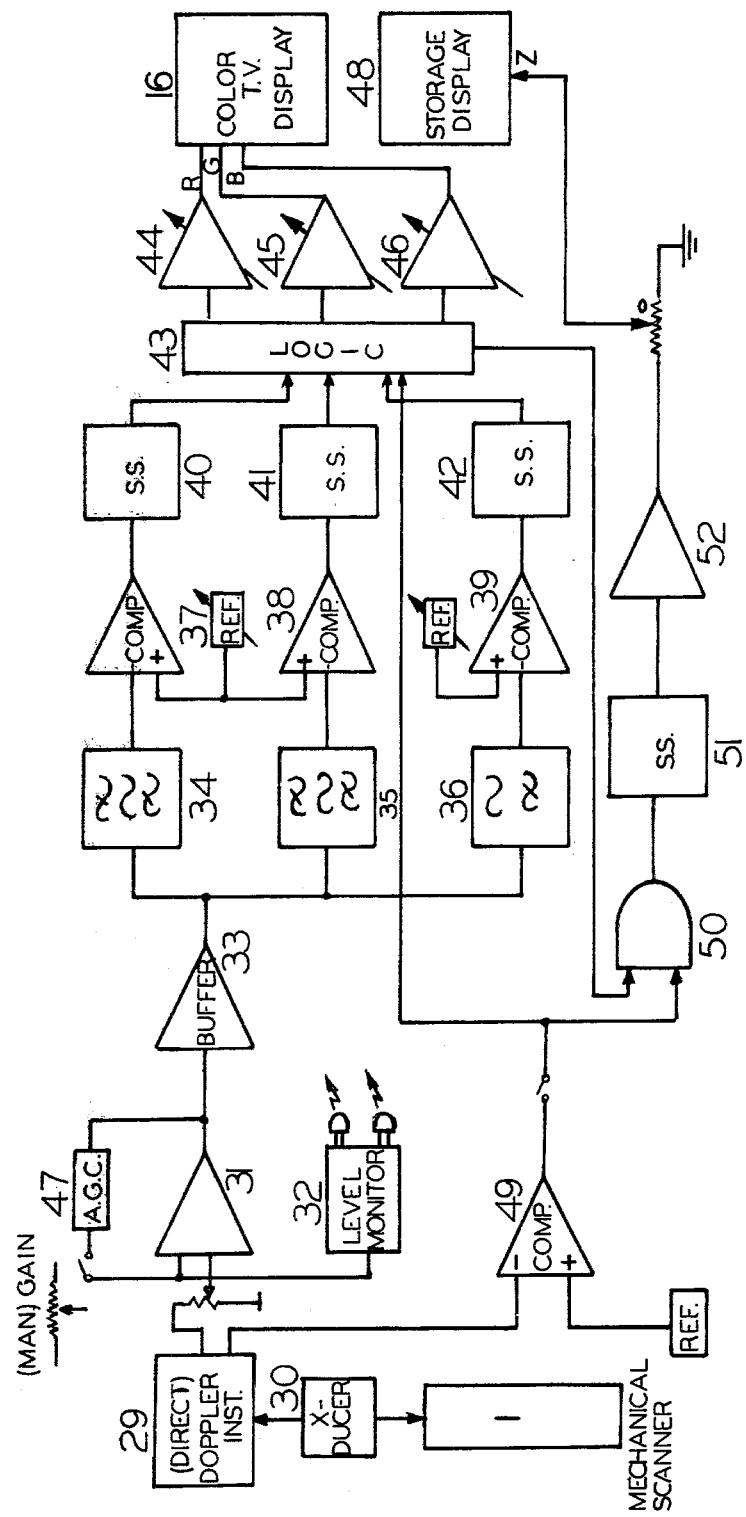

For the purpose of more fully explaining the above and still further objects and features of the invention, reference is now made to the following detailed description of a preferred embodiment thereof, together with the accompanying drawings, wherein:

FIGS. 1, 2 and 3 are circuit diagrams of the equipment of the invention.

The equipment of the present invention is based upon a conventional directional Doppler flowmeter using a zerocrossing system modified to give a separate output for anterograde and retrograde flow. The ultrasonic probe is fixed in an articulated scanning arm allowing freedom of motion only in the plane parallel to the anterolateral surface of the neck and the long axis of the carotid artery. The probe is held by the scanning arm such that its beam is inclined 45° to the long axis of the carotid artery. Scanning of the area of interest is carried out by manual motion of the probe and the attached articulated arm so that signals received during the period of scan are displayed upon both the color C.R.T. and the monitor storage C.R.T. congruously in the two lateral dimensions of the scanning plane. The Doppler shifts of the energy backscattered by the moving blood in the artery are recorded by a variable number of filtered circuits such that each circuit registers a different range of velocities of motion in either the anterograde or retrograde direction with respect to the ultrasonic probe and its beam. These various velocities are displayed as three different colors upon a conventional color C.R.T. screen in positions congruous to the position of the beam during the scan. Since the filters are set so that only peak velocities are of sufficient magnitude to activate the color display circuits, velocities from the region being insonated are only displayed for a brief period during the propagation of the arterial pulse through that segment of the artery. The total scan therefore is only slowly built up and during the whole scanning period the color display is photographed by a time exposure on quick developing color photographic film. The color display is therefore not under the observation of the operator so that, in order to ensure the area of interest is adequately and evenly scanned a monitor display upon a storage C.R.T. is also made. This monitor, of necessity, is bistable with only a black and white display and serves merely to ensure that the manual scanning movements made by the operator result in the ultrasonic beam scanning across the course of the arteries it is desired to display. When the scan is complete, as shown by the monitor display, the color photograph made from the color display is developed and inspected. During the period of the scan a simultaneous audio display is made by means of a loud-speaker which serves to help the operator scan over the area of interest from which the signals of maximal amplitude are heard most loudly. At the same time variations in the pitch of the audio signal may indicate when variations occur in the frequency of the Doppler shifted signals being detected so that the operator may have some mental image of what the color coded display that he is making but cannot see, will be like. There is however little way in which the operator can influence the color-coded image other than to optimise it by adequate scanning movements. He must, of course, use only light pressure in scanning the probe across the neck so that the artery being examined is not compressed. This has never proved to be a problem possibly because the concurrent audio display ensures that the operator continually maximises the loudness of the received signal. It might be expected that the scanning motion of the transducer across the skin might give rise to artifactual signals; this also has not proved to be a problem so long as the skin is covered with a generous layer of a coupling jelly.

As many peak velocity ranges can be displayed as desired. An appropriate filter must be assigned to each range and its frequency and frequency range chosen appropriately. Each peak velocity range can encompass as wide or narrow a range as wished. Each peak velocity range displayed can be coded by a unique and distinctive color by varying the combination of the three primary colored pixels activated by each filter. For our purposes we have found that three filters and three colors appear to be adequate. Normal peak velocities are displayed as red, moderately increased peak velocities are displayed as yellow, and markedly increased velocities as blue.

Normal velocities of flow are displayed as red. The Doppler shifted frequencies corresponding to varying velocities of peak blood flow that are displayed can cover whatever range is desired and within this range each color can represent any desired subset of frequency shifts. For our purposes the three filters in our system cover a Doppler shifted frequency range from 0.6–8 kHz. If the insonating beam is at 45° to the axial blood flow in a carotid bifurcation this range of Doppler shifted frequencies corresponds to peak velocities of flow varying from 15–210 cm.s$^{-1}$. It will be appreciated therefore that our system has a threshold below which flow is not displayed. The absence of a display therefore in any part of the carotid system being imaged means that peak flow in excess of 15 cm.s$^{-1}$ is not present in that segment of the artery; this may mean that the artery is occluded or it may mean that flow in the vessel is sluggish.

The purpose of the circuit of FIG. 1 is to locate the positive of the probe in space or scanning so that the color beams can be turned on in the displayed area of the CRT that will coincide with the (XY) co-ordinate position of the scanner. This is accomplished by DC-sampling the position of the beams during raster scanning.

The ultrasonic probe's position is read out as independent X and Y direct coupled voltages to level shift amplifiers 2 and 7. The amplifier's direct coupled output is then fed to level comparator 6, 11 respectively.

From the color T.V. display (16), vertical and horizontal sync pulses are fed to Buffer (3) and Buffer (8) respectively. Associated with the buffers are pulse shaping circuitry that provide trigger signals to one shot multivibrators 4, 9. The one shot multivibrators provide a gating period during which time integrators 5, 10, generate a linear ramp voltage for periods of 16.3 mS and 63.0 microseconds respectively.

The ramp voltages become the reference for the position of the CRT scanning beam vertically and horizontally for comparators 6, 11. The DC (XY) information from the scanner is direct coupled to the comparators 6, 11 to establish the relative position of the transducer. The voltages are such that with the probe centered upon an area of investigation, the ramp voltage triggers the comparator at half-value. The comparators then trigger single shot multivibrators 12, 13. Single shot multivibrator 12 has a duration lasting for a period of one vertical scanning interval while single shot multivibrator 13 has a duration of approximately 0.1 microseconds to 0.3 microseconds.

The output pulse of 13 is shaped and is adjustable from 0.1 microseconds to 0.3 microseconds for beam spot diameter.

And gate 14, delivers the narrow pulse formed by single shot multivibrator 13, at the appropriate time interval to an amplifier 15, which in turn drives Z-axis of color C.R.T.

The purpose of the circuit of FIG. 2 is to locate the central position of the probe, so that this area of interest will appear on the display monitor and color C.R.T. The potential area that can be covered by the mechanical scanner is so much larger than the displays that a means of locating this position and registering it in the displays was designed.

The X and Y voltages from the mechanical scanners are direct coupled to operational amplifiers 17, 22 and to output amplifiers 21, 26. The operational amplifiers 17, 22 level shift all voltages positive. Sample and hold detectors 18, 23 peak detect the positive voltages and retain their voltage until reset. These voltages are buffered by 19, 24 and fed to level shift DC amplifiers 20, 25 whose outputs are then fed to output DC amplifiers 21, 26. The original voltages coupled directly to DC amplifiers 21, 26 and the sample and detected voltages fed to 21, 26 are nearly the same, thus the output of amplifiers 21, 26 are held near zero volts, thus registering the position of the probe in the XY plane. Once the probe position has been located by pushing locate button, remote controls can then register probe position anywhere on CRT or Monitor Display. Pushing reset button will clear this reference position until a new position is located. This completes details on this part.

The circuit of FIG. 3 comprises the necessary circuitry for sampling the ultrasonic Doppler shifted signals and recording this information spatially on color polaroid film.

Directionalfdoppler flowmete9s have facilities for providing the Doppler shift signal and a voltage channel(s) for directional flow information. The Doppler shift information is taken from directional doppler instrument 29, in the form of an audio signal which is coupled to input amplifier 31. Also from instrument 29, is taken a directional voltage which is coupled to 49, a comparator. The comparator 49 is adjusted for a suitable S/N ratio. This comparator is fed through a defeat switch, to the logic unit 43 and to gate 50. With the switch on, and reverse flow is sensed, the logic unit is disabled, so that no information can be recorded by the displays.

The spectrum of audio signals, which represents the complex backscattering velocity components from the moving blood, are amplified by amp 31. Amp 31 is also under AGC (Automatic Gain Control) 47, so that signal strength variations while scanning the source tend to average out. This information is then buffered by 33 and fed to a bank of filters, but for the purposes of the accompanying diagram and description three filters are shown, 34, 35 and 36. These filters do the basic sampling of the audio spectrum and drive amplitude level detectors 37, 38, 39 if their signal strength is of sufficient amplitude. The level detectors drive single shot multivibrators whose average period is approximately 0.3 seconds.

As the arterial pressure pulse approaches the segment of artery being scanned, the blood velocity is increased substantially and it is during this period that sampling takes place. If any or all filters are detected i.e. they have sufficient signal strength, this information is transferred to the logic unit on a beat-to-beat basis.

The logic unit is synchronized by detecting output from the lowest frequency range filter 34. This synchronizing pulse also introduces a slight delay in the sampling of the single shot multivibrator 40, 41, 42 so that each filter has enough time to be registered in the logic unit. By interrogation, the logic unit 43 gives priority to the highest filter sampled, provided the filter detectors have been sensed in proper sequence. The sampling logic therefore provides some immunity from noise.

The logic unit processes all this information and drives a color coded matrix. The appropriate single shot pulse from 40, 41, 42 etc. is allowed to pass through logic unit 43 and drive the appropriate amplitude weighted amplifiers 44, 45, or 46. These amplifiers can be pulsed by the color matrix, so that any combination of colors can be used to represent a velocity range. The logic unit 43 also supplies a command pulse to gate 50 so that registration can be made on a monitor storage scope when a successful measurement has been made. A time exposure on color polaroid film is then used to record a color dot on the color CRT each time a suitable measurement has been made. In this way a two dimensional image with color-coding of velocity range can be made into a hard copy. A color monitor or a normal color TV can be used for displaying this information. A bi-stable storage oscilloscope can be used for monitoring the scanning procedure so that adequate information is acquired to prevent over or under scanning an area of interest.

The interface unit thus described is capable of displaying and recording ultrasonic Doppler shift signals that are reflected by blood flow peak velocity into a color coded display.

We claim:

1. Equipment for providing a picture of a portion of a blood vessel by a color coded display of normal and increased blood flow peak velocities at a plurality of locations within said blood vessel portion, comprising
    ultrasonic doppler scanning means including a probe providing a beam of ultrasound, said scanning means providing probe location signals relative to said blood vessel and blood flow velocity signals proportional to blood flow velocity at a location in said blood vessel
    peak velocity means for rejecting said velocity signals below a predetermined minimum and separating said velocity signals above said predetermined minimum into a plurality of selected ranges providing a plurality of independent filter means output signals representing normal and increased blood flow peak velocity ranges
    color coding means for providing a discrete color signal for each of said filter means output signals, and
    color display means responsive to said probe location signals and to said color signals for providing said color coded picture with each of said normal and increased blood flow peak velocity ranges displayed as a discrete color.

2. Equipment as claimed in claim 1, wherein
    said peak velocity filter means predetermined minimum is selected to represent less than normal blood flow peak velocity.

3. Equipment as claimed in claim 2, wherein
    said peak velocity filter means ranges are selected to represent normal, moderately increased and markedly increased blood flow peak velocity ranges, and
    said display means displays each as a discrete color, said less than normal blood flow peak velocity being characterized by the absence of a display.

4. Equipment as claimed in claim 3 wherein
    said probe is mounted for scanning movement relative to said blood vessel portion in a plane generally parallel to the long axis of said blood vessel portion and said beam is inclined at an angle to said long axis.

5. A method for providing a picture of a portion of a blood vessel by a color coded display of normal and increased blood flow peak velocities at a plurality of locations within said blood vessel portion from ultrasonic doppler velocity signals proportional to blood flow velocity at a plurality of locations in said blood vessel, comprising the steps of
    rejecting said velocity signals below a predetermined minimum
    separating said velocity signals above said predetermined minimum into a plurality of selected ranges representing normal and increased blood flow peak velocity ranges, and
    displaying each of said normal and increased blood flow peak velocity range signals as a discrete color.

* * * * *

UNITED STATES PATENT AND TRADEMARK OFFICE
CERTIFICATE OF CORRECTION

PATENT NO. : 4,205,687
DATED : June 3, 1980
INVENTOR(S) : Denis N. White et al.

It is certified that error appears in the above-identified patent and that said Letters Patent are hereby corrected as shown below:

Under References Cited, "Miora et al." should be --Miura et al.--;

Column 3, line 41, "positive" should be --position--;

Column 4, line 40, "Directionalfdoppler flowmete9s" should be --Directional doppler flowmeters--;

Column 6, line 1, after "velocity" insert --filter--;

Column 6, line 28, after "3" insert --,--.

Signed and Sealed this

Fifth Day of August 1980

[SEAL]

Attest:

SIDNEY A. DIAMOND

Attesting Officer     Commissioner of Patents and Trademarks